US005531737A

United States Patent [19]

Schade

[11] Patent Number: 5,531,737
[45] Date of Patent: Jul. 2, 1996

[54] SURGICAL X-RAY INSTRUMENT FOR GUIDING NEEDLES

[76] Inventor: Christy M. Schade, 2692 W. Walnut, Suite 105, Garland, Tex. 75042

[21] Appl. No.: 453,570

[22] Filed: May 26, 1995

Related U.S. Application Data

[63] Continuation of Ser. No. 131,723, Oct. 5, 1993, abandoned.

[51] Int. Cl.$^6$ ................................................. A61B 19/00
[52] U.S. Cl. ................................................. 606/1
[58] Field of Search .................... 606/139–148, 606/96, 99, 144, 97, 98, 103, 104, 106, 108, 130, 222, 232; 604/116, 181; 128/749–754

[56] References Cited

U.S. PATENT DOCUMENTS

| | | | |
|---|---|---|---|
| 421,919 | 2/1890 | Fergen | 606/147 |
| 2,808,054 | 10/1957 | Thayler | 606/146 |
| 4,263,903 | 4/1981 | Griggs | 606/1 |
| 4,350,151 | 9/1982 | Scott | 606/147 |
| 5,269,316 | 12/1993 | Spitalny | 128/749 |

FOREIGN PATENT DOCUMENTS 966292  10/1950  France ........................ 606/147

*Primary Examiner*—Michael H. Thaler
*Assistant Examiner*—Glenn Dawson
*Attorney, Agent, or Firm*—Baker & Botts

[57] ABSTRACT

An surgical X-ray instrument (10) is disclosed for use in guiding needles during procedures involving radiation. The instrument (10) includes a longitudinal body (12) and a handle (22). Longitudinal body (12) has a first end (18) that has at least one needle-receiving slot (14) for guiding the needle and functioning as a pointer during medical procedures using X-ray. The longitudinal body (12) is sized to allow the handle (22) to be located outside the primary radiation field. A method of manufacturing the instrument (10) is also disclosed.

16 Claims, 2 Drawing Sheets

SURGICAL X-RAY INSTRUMENT FOR GUIDING NEEDLES

CROSS REFERENCE TO RELATED APPLICATIONS

This application is a continuation of application Ser. No. 08/131,723 filed Oct. 5, 1993, entitled "Surgical X-Ray Instrument" by Cristy M. Schade, now abandoned.

TECHNICAL FIELD OF THE INVENTION

The invention relates to medical instruments, and more particularly to surgical instruments for use during medical procedures involving X-rays or radiation.

BACKGROUND OF THE INVENTION

Many medical procedures involve the precise placement of medical needles. In some medical procedures, it is desirable to place a needle into or on a specified portion of a patient's body by guiding the needle with the assistance of X-ray. For example, a discogram involves the precise placement of a needle directed by the assistance of an X-ray device or fluoroscope.

If a patient experiences pain that the physician believes to be caused by a patient's intervertebral disc, the disc may be studied by discogram, which is a procedure that entails placing a needle through the annulus fibrosus and into the nucleus pulposus of the disc. The discogram procedure is used to study the disc by injecting a radiopaque dye into the disc to study the integrity of the disc and to reproduce the patient's pain response. In performing cervical discograms, a real-time X-ray or fluoroscope is used during the procedure to allow the physician or health care provider to accurately place the needle without passing it through tissue, veins, or arteries, or nerves that might be harmful to the patient.

The discogram procedure has required the physician to use his or her hand in the primary X-ray field. In this procedure, a cervical disc may be approached from the anterior side. The physician or health care provider uses his or her index finger on the left hand (for a right-handed physician) to firmly press between the esophagus and the carotid sheath. This pressure is to locate and move as necessary the carotid artery, jugular vein, esophagus and other tissue. The discogram needle is then inserted just below the physician's left index finger. Once the needle is inserted, the fluoroscope or X-ray equipment is activated. The width of the finger separates the lateral/medial structures and under direct fluoroscopic control, the finger is used to guide the needle first to the vertebral body and then to the annulus fibrosus. The needle is then passed directly into the disc, but must not be passed through the disc. To gauge the depth of the needle, the physician advances the needle using fluoroscopy in the posterior-anterior projection and the lateral projection. The physician must spend considerable time in guiding the needle under the fluoroscope because of the potential harm of a misaligned needle; to perform this procedure, the physician may have his or her hand in the primary X-ray field for as long as ten minutes to an hour.

This technique of using one's finger to probe and guide a medical needle during a discogram has several shortcomings. First, the physician is exposed to a significant amount of radiation during the procedure. Second, the physician must place the needle against his or her index finger which increases the likelihood that the needle will puncture the physician's glove or even the physician's skin. Puncturing the physician's glove can be a serious threat to the patient because it increases the possibility that infectious contaminants may be carried into the body and particularly into the nucleus pulposus of the patient's disc, which can generate life threatening complications. Puncturing the physician's skin is dangerous because of the proliferation of the HIV virus and other diseases that may be transmitted by body fluids such as blood. Finally, the physician's finger does not make a good pointer during fluoroscopic procedures because it is not radiopaque as such.

Therefore, a need has arisen for a surgical X-ray instrument for use during medical procedures involving radiation that allows the physician to not have his hand in the primary radiation field, that reduces the risk of unwanted glove or skin puncture, and facilitates locating the needle during procedures.

SUMMARY OF THE INVENTION

The present invention provides an instrument for use in medical procedures involving radiation that eliminates or substantially reduces the shortcomings of the prior art techniques. The present invention provides an instrument for assisting a physician with the placement of a needle on a specified portion of the patient's body during procedures involving radiation. The instrument includes a longitudinal body that has a first needle-receiving channel or slot located on a first end of the longitudinal body, which is placed against the patient during procedures. The longitudinal body may have a handle coupled to it that assists the physician in holding and controlling the instrument during procedures. The longitudinal body of the instrument may be sized to keep the physician's hand outside the primary field of radiation.

In accordance with another aspect of the present invention, a second needle-receiving channel or slot can be located on the first end of the longitudinal body. This second needle-receiving channel may be used during fluoroscopy as a pointer or to receive and guide a second needle.

In accordance with another aspect of the present invention, a method of manufacturing a surgical X-ray instrument is provided. The method includes providing a longitudinal member formed with a first needle-receiving slot and coupling a handle for holding and controlling the instrument to the longitudinal member. A second needle-receiving slot may also be formed in the longitudinal member.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
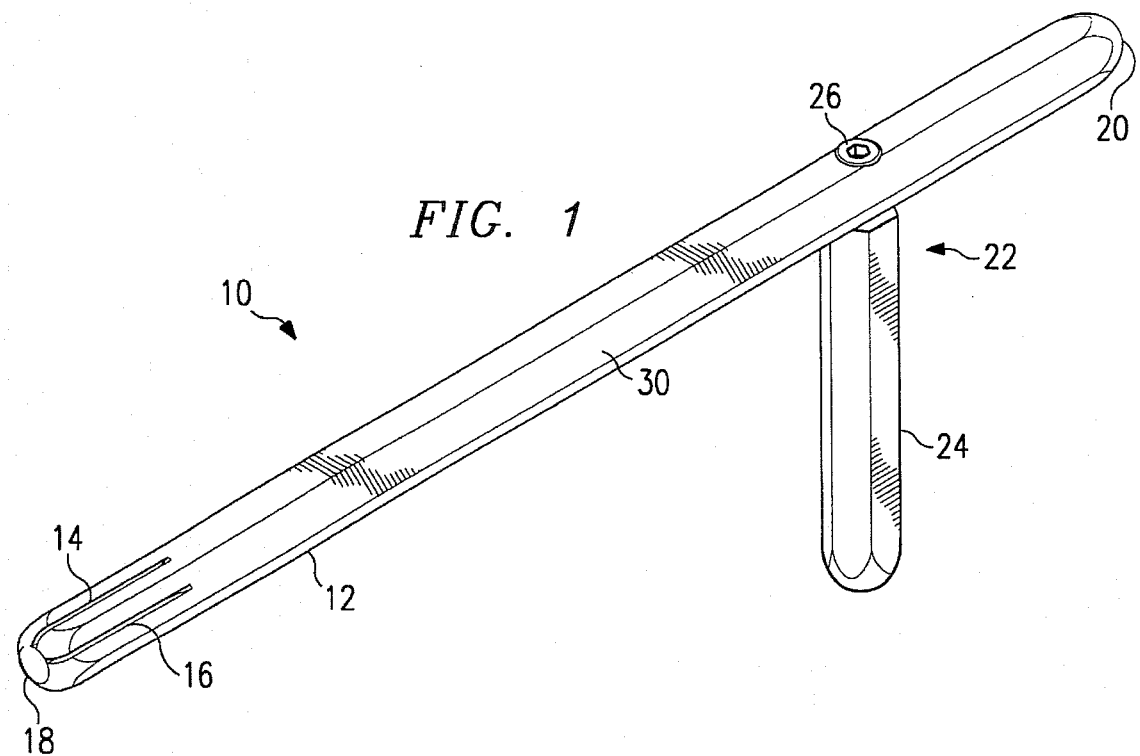
FIG. 1 is a perspective view of one embodiment of the surgical instrument of the present invention.
Figure 2:
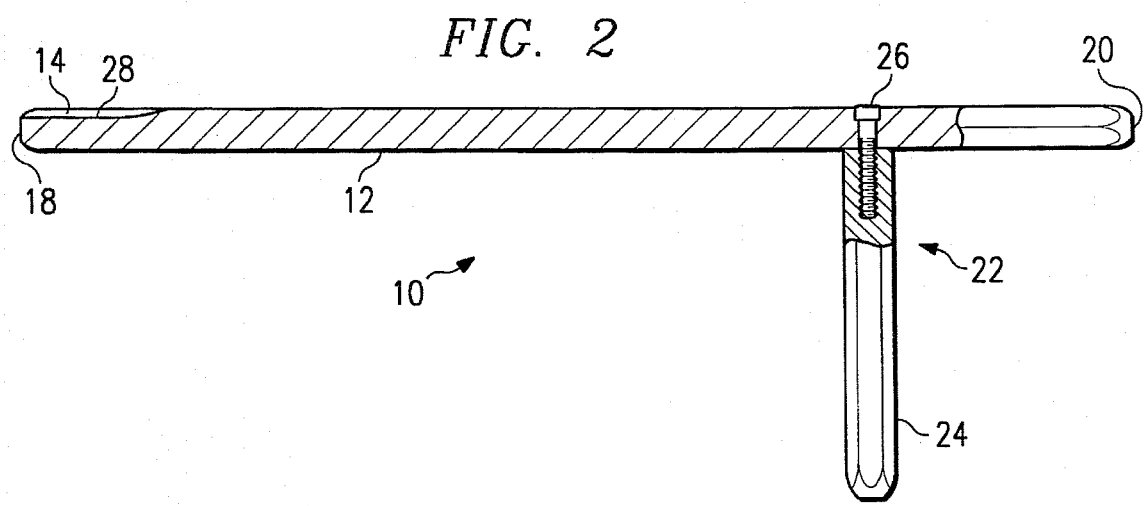
FIG. 2 is a schematic cross-sectional view in elevation of the surgical instrument of FIG. 1.
Figure 3:
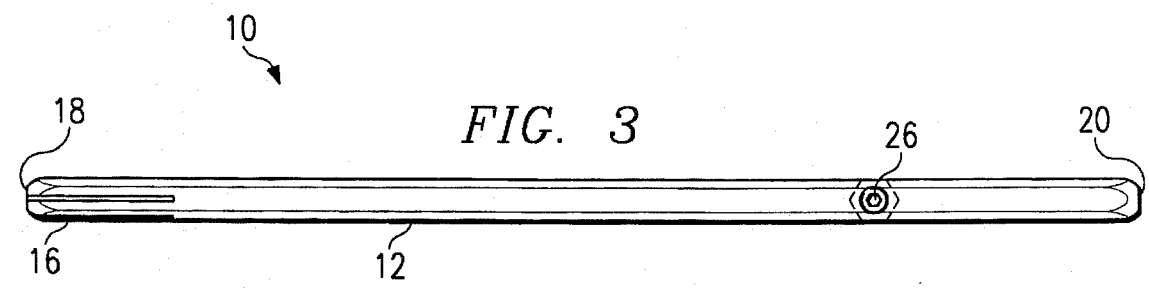
FIG. 3 is a schematic plan view of the surgical instrument of FIGS. 1 and 2.

The preferred embodiment of the present invention and its advantages are best understood by referring to FIGS. 1–3 of the drawings, like numerals being used for like and corresponding parts of the various drawings.

Referring to FIG. 1, there is shown surgical X-ray instrument 10. Instrument 10 has a central longitudinal member or body 12. Longitudinal body 12 is formed to have a first needle-receiving channel or slot 14 and may have a second needle-receiving/pointer channel or slot 16. Channels or slots 14 and 16 are formed on a first end 18 of longitudinal body 12. First end 18 of longitudinal body 12 is the portion of instrument 10 that is placed against the skin or other body part of the patient during procedures using instrument 10. Longitudinal body 12 has a second end 20 that is opposite from first end 18. Handle 22 is coupled or attached to longitudinal body 12. Handle 22 allows the physician to hold instrument 10 and to control instrument 10 in terms of pressure and angular position. Handle 22 may be gripping bar 24 which is shown attached perpendicularly to longitudinal body 12 by fastener 26.

Longitudinal member 12 may be formed of a radiopaque material. A radiopaque material is a material that is not appreciably penetrable by X-rays or other forms of radiation. Thus, when used with a fluoroscope, longitudinal body 12 will be visible. A fluoroscope is a fluorescent screen designed for use with an X-ray tube to permit direct real-time visual observation of X-ray shadow images of objects interposed between the X-ray tube and the screen.

In the preferred embodiment, longitudinal member 12 and gripping bar 24 are made of aluminum or stainless steel. The preferred manner of sterilizing instrument 10 is with use of an autoclave, and therefore, any radiopaque material used to form instrument 10 must be able to withstand the high temperatures involved with autoclaves and able to withstand the wet environment involved with autoclaves, i.e., have a slow oxidation rate.

Figure 4:
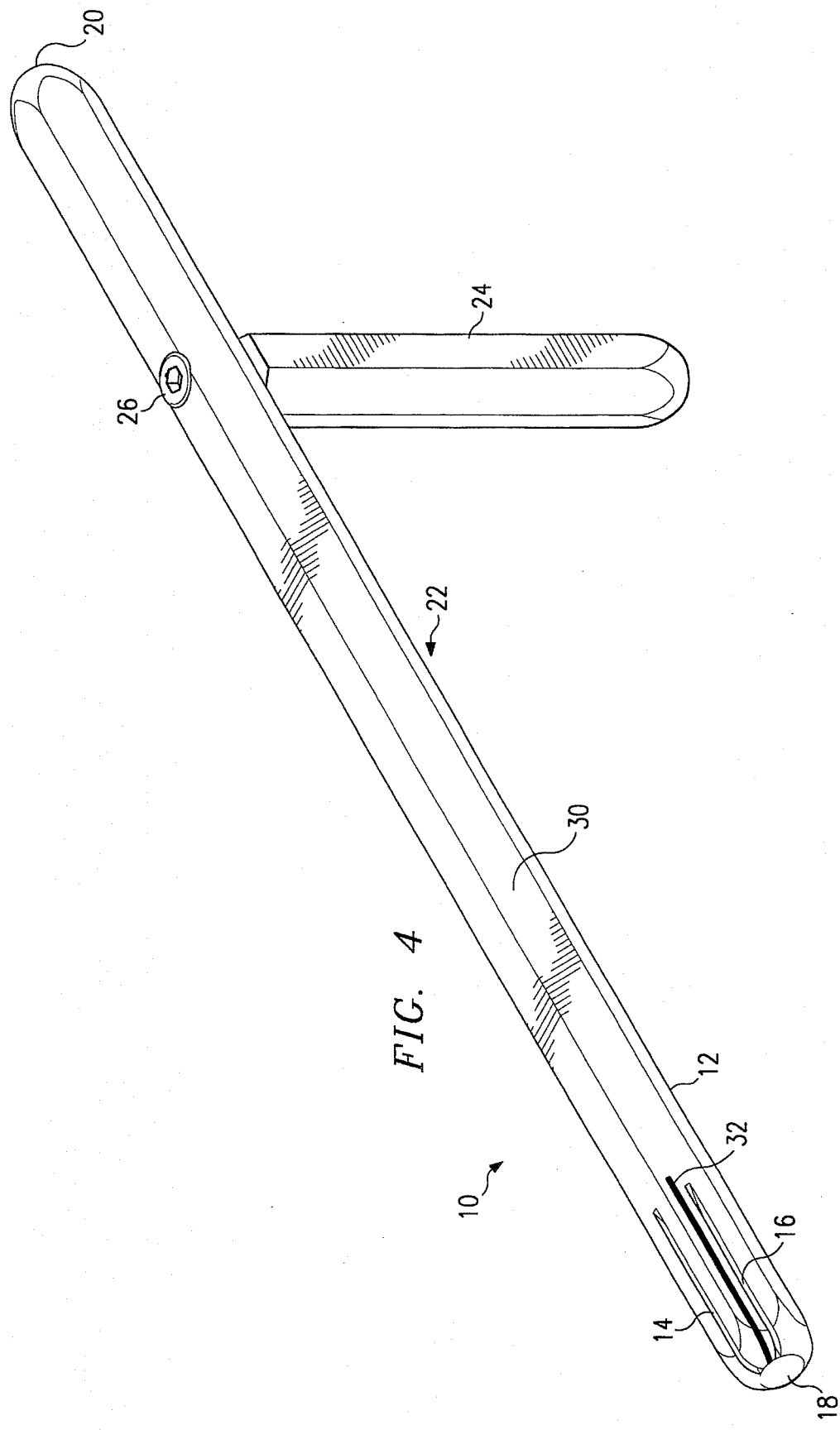
FIG. 4 is a perspective view of another embodiment of the surgical instrument of the present invention.

In an alternative embodiment shown in FIG. 4, a synthetic material such as a hard plastic may be used to form longitudinal body 12. In this alternative embodiment, a radiopaque member 32 may be attached to first end 18 of longitudinal body 12 or the core of longitudinal body 12 formed of a radiopaque material to allow first end 18 to be viewed on the fluoroscope. Another method of sterilization is to use a gas sterilizer. Therefore, the synthetic material must not react with or trap the sterilizing gas when sterilized by a gas sterilizer.

First end 18 of longitudinal body 12 is designed to move the jugular vein, carotid artery, esophagus, and tissue in a manner similar to how a physician used his finger in the prior art techniques. Because of the pressure that must be applied to first end 18 against the patient's neck or other body part, it is desirable to form first end 18 to maximize the comfort of the patient. In the preferred embodiment, first end 18 has been rounded to a finger-like shape. The rounded corners of first end 18 of longitudinal body 12 help distribute stresses and eliminates high pressure points on the patient's skin or body part, and thereby makes the instrument more comfortable to the patient.

First needle-receiving slot 14 is sized to receive a medical needle used in a procedure (not shown). In a cervical discogram, a twenty-five or twenty-three gauge needle is used to pass through the patient's skin, through the annulus fibrosus, and into the nucleus pulposus. In performing procedures such as the cervical discogram, the needle must be placed with extreme accuracy, and it is important for the physician to know exactly where the needle is aligned. To facilitate locating the needle with the necessary precision, the first needle-receiving channel or slot 14 is formed so that when the needle is passed into slot 14 and pressed against slot 14, the needle will exit first end 18 of longitudinal body 12 substantially parallel to the longitudinal axis of longitudinal body 12.

Referring to the cross-sectional view of FIG. 2, the internal portion of slot 14 may be viewed. As a medical needle is placed into slot 14 farthest from first end 18 and pressed against slot 14, the needle bends slightly and as it is moved in the direction of first end 18, the needle conforms to bottom surface 28 of slot 14. Because bottom surface 28 is substantially parallel to the longitudinal axis of longitudinal body 12, the needle will likewise exit first end 18 with this orientation.

Second needle-receiving/pointer slot or channel 16 is provided in longitudinal body 12 for the purpose of providing a pointer in instrument 10. Needle receiving slot 14 is also used for passing a needle to administer a local anesthesia when needed. The anesthesia-administering needle is typically a shorter needle that will infiltrate the skin with a local anesthetic to numb the skin. The use of slot 14 allows the longer needle to be passed in exactly the same spot that was anesthetized by the shorter needle. As shown in FIG. 3, second needle-receiving slot 16 may be located approximately forty-five degrees to first needle-receiving slot 14.

X-ray devices used in many medical techniques, including the discogram, create primary and secondary radiation fields. Longitudinal body 12 is sized to have a length great enough to allow placement of first end 18 at the necessary point with respect to the primary X-ray field, to allow handle 22, which is located proximate second end 20, to be outside the primary X-ray field. Thus, during procedures, the physician's hand on handle 22 will not be in the primary X-ray field. Secondary radiation may be associated with the use of the primary radiation field because of such things as Compton scattering.

To further shield the physician's hand on handle 22, a radiation shield (not shown) may be attached to longitudinal body 12 between first end 18 and handle 22 in order to shield the physician's hand from secondary radiation. The radiation shield may be, for example, a light weight lead cup mounted on longitudinal body 12 in a manner similar to the hand protectors on swords of days of old.

To manufacture instrument 10, a manufacturer may provide longitudinal member 12, which may be formed of a radiopaque material, then form first and second needle-receiving slots 14 and 16 on first end 18 of longitudinal body 12. The manufacturer may then provide handle 22 on longitudinal body 12 near or proximate second end 20. First slot 14 is formed so that when a needle is passed through slot 14, it will exit approximately parallel to longitudinal axis of longitudinal body 12.

Gripping bar 24 may be attached to longitudinal body 12 by use of fastener 26. As shown in FIG. 2, the fastener may be a screw 26 passing through longitudinal body 12 and into gripping bar 24. In the alternative, the gripping bar 24 could be welded to longitudinal body 12.

As an example of how instrument 10 might be used, the use of instrument 10 to perform a discogram will be described. The physician or health care provider begins by placing their hand on gripping bar 24. For a right handed physician, his or her left hand will be put on gripping bar 24. Gripping bar 24 will be placed on the palm of the physician's hand, and the physician's index finger placed along longitudinal body 12 near the region shown by reference numeral 30 (FIG. 1). The physician first places first end 18 of instrument 10 on the patient's neck between the esophagus/trachea and the carotid sheath. The fluoroscope or other real-time X-ray equipment may then be activated. Needle-receiving slot 16 and the radiopaque material of longitudinal body 12 allow instrument 10 to function as a pointer on the fluoroscope. The physician then uses the rounded first end 18 of instrument 10 to position and move the jugular vein, carotid artery, esophagus and other tissues so that the needle may pass to the desired disc without puncturing these body parts. An anesthesia-delivering short needle may then be passed into needle-receiving slot 14 to administer a local anesthesia. The physician then places the long disk-penetrating needle into slot 14 farthest from first end 18 and slides the needle towards first end 18. The physician continues this motion until the needle has passed into the patient's body, and then, using precise surgical techniques and the benefit of instrument 10 compressing the tissues and functioning as a pointer, the physician places the needle into the nucleus pulposus. The instrument is then withdrawn leaving the needle in the disc. Needles may be placed in multiple discs using this technique. After all the needles have been placed in the discs, then the physician administers the radiopaque dye as discussed in the background of the invention section.

When the procedure is complete, the physician then removes the needle or needles from the patient's body. During the discogram procedure, instrument 10 is gripped by the left hand of the right-handed physician, while the physician's right hand is used to administer the needles through slot 14.

Although the present invention and its advantages have been described in detail, it should be understood that various changes, substitutions and alterations can be made therein without departing from the spirit and scope of the invention as defined by the appended claims.

What is claimed is:

1. An instrument for assisting a physician with the placement of a needle on a specified portion of a patient's body during procedures involving radiation, the instrument comprising:

a unitary, longitudinal body having a first end, a second end, an outer surface defining a periphery of said longitudinal body and a longitudinal axis, the longitudinal body formed to have a first needle-receiving slot located substantially at the first end of the longitudinal body sized end configured for receiving and directing the needle substantially parallel to the longitudinal axis of the longitudinal body, said outer surface of said longitudinal body remaining substantially constant while said needle is directed substantially parallel to the longitudinal axis, the needle-receiving slot extending from an exterior surface of the longitudinal body to the first end of the longitudinal body;

a handle coupled to the longitudinal body proximate the second end of the longitudinal body, the handle for holding and controlling the instrument by the physician; and a second needle-receiving slot located substantially at the first end of the longitudinal body and circumferentially offset with respect to said first needle-receiving slot along the periphery of said longitudinal body; wherein the longitudinal body sized so that the handle is located outside a primary area of the radiation during the procedure; and wherein said first needle-receiving slot secured without movement on said longitudinal body with respect to said handle.

2. The instrument of claim 1, wherein the longitudinal body is formed of a radiopaque material.

3. The instrument of claim 2, wherein the radiopaque material comprises stainless steel.

4. The instrument of claim 2, wherein the radiopaque material comprises aluminum.

5. The instrument of claim 1, wherein the first end of the longitudinal body comprises a rounded surface.

6. The instrument of claim 1, wherein the handle comprises a gripping bar and wherein the gripping bar is attached to the longitudinal body approximately perpendicular to the longitudinal body.

7. A surgical instrument for facilitating placement of a first needle into a specified portion of a patient's body by a health care provider during procedures involving X-ray radiation, the instrument comprising:

a longitudinal body having a first end, a second end, a longitudinal axis and an outer surface defining a periphery of said longitudinal body;

a first slot formed substantially on the first end of the longitudinal body being sized and configured for receiving the first needle and directing the first needle substantially parallel to the longitudinal body, said outer surface of said longitudinal body remaining substantially constant while said needle is directed substantially parallel to the longitudinal axis, the slot extending from the outer surface of the longitudinal body to the first end of the longitudinal body;

a second needle-receiving slot located substantially at the first end of the longitudinal body and circumferentially offset with respect to said first needle-receiving slot along the periphery of said longitudinal body; and a handle attached proximate the second end of the longitudinal body for gripping and controlling the instrument by the health care provider; wherein said first needle-receiving slot secured without movement on said longitudinal body with respect to said handle.

8. The instrument of claim 7, wherein the first end of the longitudinal body comprises a rounded end.

9. The instrument of claim 7, wherein the longitudinal body is formed of a synthetic material.

10. The instrument of claim 9 further comprising a radiopaque member coupled to the longitudinal body, the radiopaque member for allowing the first end of the longitudinal body to be viewed on an X-ray device.

11. The instrument of claim 7 wherein the longitudinal body comprises a radiopaque material.

12. The instrument of claim 7 wherein the longitudinal body comprises aluminum.

13. A method of manufacturing a surgical instrument for allowing a physician to direct a first needle onto a specified portion of a patient's body during procedures using radiation, the method comprising the steps of:

providing a longitudinal member formed of a radiopaque material, said longitudinal member having a longitudinal axis and comprising a first end, a second end and a substantially constant outer surface defining a periphery of said longitudinal body;

forming a first needle-receiving slot on substantially a first end of the longitudinal member;

providing a handle for holding and controlling the instrument by the physician;

coupling the handle to a second end of the longitudinal member, said needle receiving slot secured without movement on said longitudinal member with respect to said handle;

forming a second needle-receiving slot on the first end of the longitudinal member, said second needle-receiving slot circumferentially offset on said longitudinal member with respect to said first needle receiving slot; said slots sized and configured for receiving a directing a needle generally parallel to the longitudinal axis; and providing a pointer on the first end of the longitudinal member.

14. The method of claim 13 further comprising the step of: rounding the first end of the longitudinal body to proximate a human finger tip.

15. The method of claim 13, wherein the step of providing a handle comprises providing a gripping bar.

16. The method of claim 15, wherein the step of coupling the handle comprises perpendicularly attaching the gripping bar with a fastener proximate the second end of the longitudinal member.

* * * * *

UNITED STATES PATENT AND TRADEMARK OFFICE
CERTIFICATE OF CORRECTION

PATENT NO. : 5,531,737
DATED : Jul. 2, 1996
INVENTOR(S) : Schade

It is certified that error appears in the above-identified patent and that said Letters Patent is hereby corrected as shown below:

Title Page, [56], U.S. PATENT DOCUMENTS after "2,808,054 10/1957" delete "Thayler" and insert -- Thayer --;

Title Page, [76], after "Inventor:", delete "Christy" and insert -- Cristy --.

Column 5, line 44, after "sized", delete "end" and insert -- and --.

Column 7, line 3, after "receiving" delete "a" and insert -- and--.

Signed and Sealed this

Twenty-first Day of January, 1997

Attest:

BRUCE LEHMAN

*Attesting Officer*  *Commissioner of Patents and Trademarks*